(12) United States Patent
Cristalli

(10) Patent No.: US 6,914,053 B2
(45) Date of Patent: Jul. 5, 2005

(54) ADENOSINE $A_3$ RECEPTOR AGONISTS

(75) Inventor: Gloria Cristalli, Camerino (IT)

(73) Assignee: CV Therapeutics, Inc., Palo Alto, CA (US)

( * ) Notice: Subject to any disclaimer, the term of this patent is extended or adjusted under 35 U.S.C. 154(b) by 0 days.

(21) Appl. No.: 10/657,762

(22) Filed: Sep. 8, 2003

(65) Prior Publication Data

US 2004/0121978 A1 Jun. 24, 2004

Related U.S. Application Data

(60) Provisional application No. 60/409,424, filed on Sep. 9, 2002.

(51) Int. Cl.[7] .................. A61K 31/70; C07H 19/167
(52) U.S. Cl. .................. 514/46; 536/27.23; 536/27.61; 536/27.63
(58) Field of Search .................. 536/27.23, 27.61, 536/27.63; 514/46

(56) References Cited

U.S. PATENT DOCUMENTS

2003/0078232 A1 4/2003 Elzein et al.

FOREIGN PATENT DOCUMENTS

| WO | WO 00/78777 A1 | 12/2000 |
| WO | WO 00/78778 A3 | 12/2000 |
| WO | WO 00/78778 A2 | 12/2000 |
| WO | WO 00/78779 A3 | 12/2000 |
| WO | WO 00/78779 A2 | 12/2000 |

OTHER PUBLICATIONS

(R) Volpini et al., "N6–Alkyl–2–alkynyl Derivatives of Adenosine as Potent and Selective Agonists at the Human Adenosine A3 Receptor and a Starting Point for Searching A2B Ligands," Journal of Medicinal Chemistry, 45(15), 3271–3279 (Jul. 18, 2002).*
(S) Baraldi et al., "Synthesis and and Biological Activity of a New Series of N6–Arylcarbamoyl, 2(Ar)alkynyl–N6–arylcarbamoyl, and N6–Carboxamido Derivatives . . . ," Journal of Medicinal Chemistry, 41(17), 3174–3185 (Aug. 13, 1998).*
(T) Siddiqi et al., "Search for New Purine– and Ribose–Modified Adenosine Analogues as Selective Agonists and Antagonists a Adenosine Receptors, " Journal of Medicinal Chemistry, 38(7), 1174–1188 (Mar. 31, 1995).*
(U) Klotz et al. (I), "2–Substituted N–ethylcarboxamidoadenosine Derivatives as High–Affinity Agonists at A3 Adenosine Receptors," Naunyn–Schmiedeberg's Archives of Pharmacology, 360(2), 103–108 (1999); published online on Jul. 13, 1999.*
(V) Klotz et al. (II), "Comparative Pharmacology of Human Adenosine Receptor Subtypes—Characterization of Stably Transfected Receptors in CHO Cells," Naunyn–Schmiedeberg's Archives of Pharmacology, 357(1), 1–9 (1998).*
(W) Stu Borman, "A3 Receptors," Science & Technology Section of Chemical & Engineering News, 79(7), 37–40 (Feb. 12, 2001).*

Volpini et al., "N[6]–Alkyl–2–alkynyl Derivatives of Adenosine as Potent and Selective Agonists at the Human Adenosine $A_3$ Receptor and a Starting Point for Searching $A_{2B}$ Ligands," Journal of Medicinal Chemistry, 45 (15), 3271–3279 (Jul. 18, 2002).

Baraldi et al., "Synthesis and and Biological Activity of a New Series of N[6]–Arylcarbamoyl, 2(Ar)alkynyl–N[6]–arylcarbamoyl, and N[6]–Carboxamido Derivatives of Adenosine–5'–N–ethyluronamide as $A_1$ and $A_3$ Adenosine Receptor Agonists," Journal of Medicinal Chemistry, 41 (17), 3174–3185 (Aug. 13, 1998).

(Continued)

Primary Examiner—James O. Wilson
Assistant Examiner—L. E. Crane
(74) Attorney, Agent, or Firm—Brian Lewis; J. Elin Hartrum; Pauline Ann Clarke

(57) ABSTRACT

Disclosed are novel adenosine $A_3$ receptor agonists of Formula I:

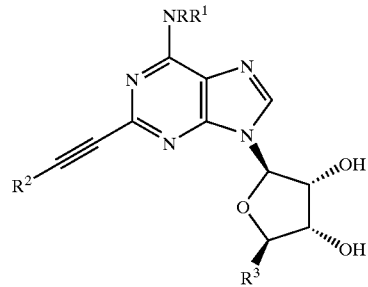

Formula I wherein:

R is hydrogen or lower alkyl;

$R^1$ is optionally substituted lower alkoxy or optionally substituted cycloalkyloxy;

$R^2$ is hydrogen, optionally substituted alkyl, optionally substituted cycloalkyl, optionally substituted aryl, optionally substituted heteroaryl, or optionally substituted trialkylsilyl; and $R^3$ is hydroxymethyl or $R^4R^5NC(Q)$—;

in which $R^4$ and $R^5$ are hydrogen, optionally substituted alkyl, optionally substituted cycloalkyl, optionally substituted heterocyclyl, optionally substituted aryl, or optionally substituted heteroaryl.

24 Claims, No Drawings

OTHER PUBLICATIONS

Siddiqi et al., "Search for New Purine– and Ribose–Modified Adenosine Analogues as Selective Agonists and Antagonists at Adenosine Receptors," *Journal of Medicinal Chemistry, 38* (7), 1174–1188 (Mar. 31, 1995).

Klotz et al. (I), "2–Substituted N–ethylcarboxamidoadenosine Derivatives as High–Affinity Agonists at $A_3$ Adenosine Receptors," *Naunyn–Schmiedeberg's Archives of Pharmacology, 360* (2), 103–108 (1999); published online on Jul. 13, 1999.

Klotz et al. (II), "Comparative Pharmacology of Human Adenosine Receptor Subtypes—Characterization of Stably Transfected Receptors in CHO Cells," *Naunyn–Schmiedeberg's Archives of Pharmacology, 357* (1), 1–9 (1998).

Stu Borman, "$A_3$ Receptors," Science & Technology Section of *Chemical & Engineering News, 79* (7), 37–40 (Feb. 12, 2001).

Klotz et al: "2–Substituted N–Ethylcarboxamidoadenosine Derivatives as High–Affinity Agonists at Human A3 Adenosine Receptors", Nauny–Schmiedeberg's Archives of Pharmacology, Springer, Berlin, DE., vol. 360, No. 2, 1999, pp. 103–108 XP000984051, ISSN: 0028–1298, compound 8, tables 1,2 (Jul. 13, 1999).

Baraldi et al: "Novel N6-(Substituted–phenylcarbamoyl) Adenosine–5'–Uronamides as Potent Agonist for A2 Adenosine Receptors", Journal of Medicinal Chemistry, American Chemical Society, Washington, US, vol. 39, No. 3, (Feb. 1996), pp. 802–806, XP002913657, ISSN: 0022–2623, conclusions on p. 804, pp. 803, col. 2, paragraph 4; (Publ. ACS Abstr; Dec. 15, 1995).

* cited by examiner

ADENOSINE $A_3$ RECEPTOR AGONISTS

Priority is claimed to U.S. Provisional Patent Application Ser. No. 60/409,424, filed Sep. 9, 2002, the complete disclosure of which are hereby incorporated by reference.

FIELD OF THE INVENTION

This invention relates to novel $A_3$ adenosine receptor agonists that are useful in the treatment of neurological and cardiac ischemia, asthma, leukopenia and neutropenia, cancer and inflammation. The invention also relates to methods for the preparation of such compounds, and to pharmaceutical compositions containing them.

BACKGROUND

Adenosine is a naturally occurring nucleoside that exerts its biological effects by interacting with a family of adenosine receptors identified as the adenosine $A_1$, $A_{2a}$, $A_{2b}$, and $A_3$ receptors, all of which modulate important physiological processes. For example, stimulation of the adenosine $A_1$ receptors shortens the duration and decreases the amplitude of the action potential of AV nodal cells, and hence prolongs the refractory period of the AV nodal cell. Thus, stimulation of adenosine $A_1$ receptors provides a method of treating supraventricular tachycardias, including termination of nodal re-entrant tachycardias, and control of ventricular rate during atrial fibrillation and flutter. Adenosine $A_{2A}$ receptors modulate coronary vasodilation, adenosine $A_{2B}$ receptors have been implicated in mast cell activation, asthma, vasodilation, regulation of cell growth, intestinal function, and modulation of neurosecretion (See Adenosine $A_{2B}$ Receptors as Therapeutic Targets, Drug Dev Res 45:198; Feoktistov et al., Trends Pharmacol Sci 19:148–153).

$A_3$ adenosine receptors modulate a variety of biological processes. In particular, compounds that are $A_3$ adenosine receptor agonists have utility in the therapeutic and/or prophylactic treatment of cancer, cardiac disease, infertility, kidney disease, and CNS disorders. Additionally, $A_3$ adenosine receptor agonists stimulate the secretion of G-CSF, a cytokine involved with the growth and differentiation of bone marrow cells. Accordingly, $A_3$ adenosine receptor agonists are useful for countering the cytotoxic side effect of drugs, in particular chemotherapeutic drugs, such as leukopenia and neutropenia.

Few ligands for the $A_3$ adenosine receptor have been reported. A non-selective $N^6$-substituted adenosine derivatives, known as APNEA ($N^6$-2-(4-aminophenyl) ethyladenosine, was reported by Zhou (Zhou et al. 1992. PNAS. 89(16):7432). Such compounds have been used experimentally but provide no therapeutic benefit. Also, 2-alkynyl-N6-substituted adenosines that are agonists at the $A_3$ adenosine receptor have been produced. (Cristalli et al. 2000. Drug Dev. Res. 50(1):072.

Accordingly, it is desired to provide compounds that are $A_3$ adenosine receptor agonists. Preferably, the compounds would be selective for the $A_3$ adenosine receptor, thus avoiding side effects caused by interaction with other adenosine receptors.

SUMMARY OF THE INVENTION

It is an object of this invention to provide $A_3$ adenosine receptor agonists. Accordingly, in a first aspect, the invention relates to compounds of Formula I:

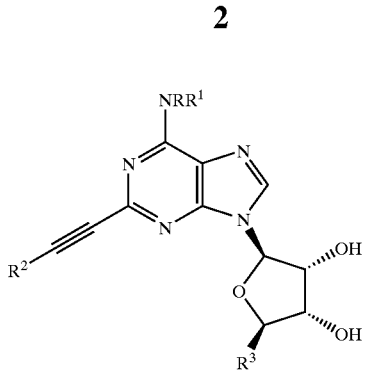

Formula I wherein:
R is hydrogen or lower alkyl;
$R^1$ is optionally substituted lower alkoxy or optionally substituted cycloalkyloxy;
$R^2$ is hydrogen, optionally substituted alkyl, optionally substituted cycloalkyl, optionally substituted aryl, optionally substituted heteroaryl, or optionally substituted trialkylsilyl; and
$R^3$ is hydroxymethyl or $R^4R^5NC(O)$—;
in which $R^4$ and $R^5$ are hydrogen, optionally substituted alkyl, optionally substituted cycloalkyl, optionally substituted heterocyclyl, optionally substituted aryl, or optionally substituted heteroaryl:
and the pharmaceutically acceptable salts, esters and prodrugs thereof.

A second aspect of this invention relates to pharmaceutical formulations, comprising a therapeutically effective amount of a compound of Formula I and at least one pharmaceutically acceptable excipient.

A third aspect of this invention relates to a method of using the compounds of Formula I in the treatment of a disease or condition in a mammal that is treatable with an $A_3$ adenosine receptor agonist, comprising administering to a mammal in need thereof a therapeutically effective dose of a compound of Formula I. Such diseases include, but are not limited to neurological and cardiac ischemia, asthma, leukopenia and neutropenia, cancer and inflammation.

A fourth aspect of this invention relates to methods of preparing the compounds of Formula I.

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl,n-decyl, tetradecyl, and the like.

The term "substituted alkyl" refers to:
1) an alkyl group as defined above, having 1, 2, 3, 4 or 5 substituents, preferably 1 to3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or 2) an alkyl group as defined above that is interrupted by 1–10 atoms independently chosen from oxygen, sulfur and and NR$_a$—, where Ra is chosen from hydrogen, optionally substituted alkyl, cycloalkyl, cycloalkenyl, aryl, heteroaryl and heterocycyl, or groups selected from carbonyl, carboxyester, carboxyamide and sulfonyl. All substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or (3) an alkyl group as defined above that has both 1, 2, 3, 4 or 5 substituents as defined above and is also interrupted by 1–10 atoms as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, for example 1, 2, or 3 substituents, as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, for example having from 1 to 20 carbon atoms, preferably 1–10 carbon atoms, more preferably 1, 2, 3, 4, 5 or 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain, for example having from 1, 2, 3, 4, 5, or 6 carbon atoms.

The term "substituted alkylene" refers to:

(1) an alkylene group as defined above having 1, 2, 3, 4, or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO$_2$-alkyl, —SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or (2) an alkylene group as defined above that is interrupted by 1–20 atoms independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or (3) an alkylene group as defined above that has both 1, 2, 3, 4 or 5 substituents as defined above and is also interrupted by 1–20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers(—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "optionally substituted lower alkoxy" refers to the group R—O—, where R is optionally substituted lower alkyl as defined above, and the term "optionally substituted lower cycloalkyloxy" refers to the group R—O—, where R is optionally substituted cycloalkyl of 3–6 carbon atoms, optionally substituted as defined below. Preferred are lower alkoxy groups, which include methoxy, ethoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1–6, preferably 1, double bond (vinyl). Preferred alkenyl groups include ethenyl or vinyl (—CH═CH$_2$), 1-propylene or allyl (—CH$_2$CH═CH$_2$), isopropylene (—C(CH$_3$)═CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1, or 2.

The term "alkynyl" refers to a monoradical of an unsaturated hydrocarbon, preferably having from 2 to 20 carbon atoms, more- preferably 2 to 10 carbon atoms and even more preferably 2 to 6 carbon atoms and having at least 1 and preferably from 1–6 sites of acetylene (triple bond) unsaturation. Preferred alkynyl groups include ethynyl, (—C≡CH), propargyl (or propynyl, —C≡CCH$_3$), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1, or 2.

The term "aminocarbonyl" refers to the group —C(O)NRR where each R is independently hydrogen, alkyl, cycloalkyl, aryl, heteroaryl, heterocyclyl or where both R groups are joined to form a heterocyclic group (e.g., morpholino). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R, is alkyl, aryl, or heteroaryl and n is 0, 1 or 2.

The term "ester" or "carboxyester" refers to the group —C(O)OR, where R is alkyl, cycloalkyl, aryl, heteroaryl, or heterocyclyl, which may be optionally further substituted by alkyl, alkoxy, halogen, CF$_3$, amino, substituted amino, cyano, or —S(O)$_n$R$_a$, in which R$_a$ is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with 1, 2, 3, 4 or 5 substituents, preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_{O2}$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, aryl, heteroaryl and heterocyclyl provided that both R groups are not hydrogen, or a group —Y—Z, in which Y is optionally substituted alkylene and Z is alkenyl, cycloalkenyl, or alkynyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or2.

The term "carboxyalkyl" refers to the groups —C(O)O-alkyl, —C(O)O-cycloalkyl, where alkyl and cycloalkyl, are as defined herein, and may be optionally further substituted by alkyl, alkenyl, alkynyl, alkoxy, halogen, CF$_3$, amino, substituted amino, cyano, or —S(O)$_n$R, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "substituted cycloalkyl" refers to cycloalkyl groups having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, preferably 1, 2, or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl (an alkyl ester), arylthio, heteroaryl, heteroarylthio, heterocyclylthio, thiol, alkylthio, aryl, aryloxy, aralkyl, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, S$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Heterocyclic groups can have a single ring or multiple condensed rings. Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH. "Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed and polymorphs thereof, pharmaceutically acceptable salts, pharmaceutically acceptable esters, and prodrugs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:
(i) preventing the disease, that is, causing the clinical symptoms of the disease not to develop;
(ii) inhibiting the disease, that is, arresting the development of clinical symptoms; and/or
(iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and triamines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Nomeclature

The naming and numbering of the compounds of the invention is illustrated with a representative compound of Formula I in which R is hydrogen, $R^1$ is methoxy, $R^2$ is 4-methoxyphenyl and $R^3$ is hydroxymethyl:

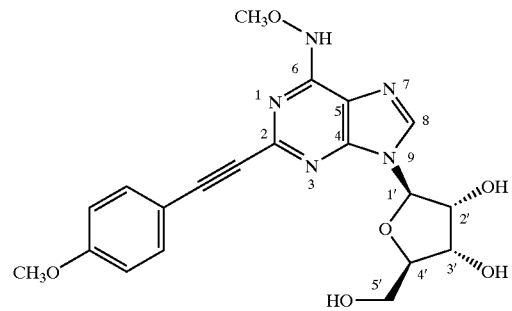

which is named: (4S,2R,3R,5R)-5-(hydroxymethyl)-2-{6-(methoxyamino)-2-[2-(4-methoxyphenyl)ethynyl]purin-9-yl}oxolane-3,4-diol.

Synthesis of the Compounds of Formula I

One method for preparing the compounds of Formula I where $R^3$ is hydroxymethyl is shown in Reaction Scheme I.

REACTION SCHEME I

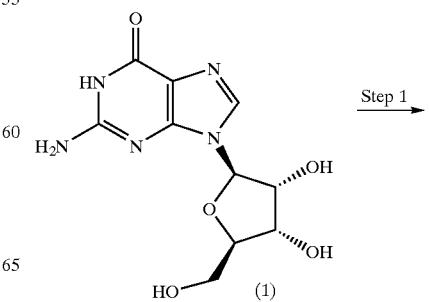

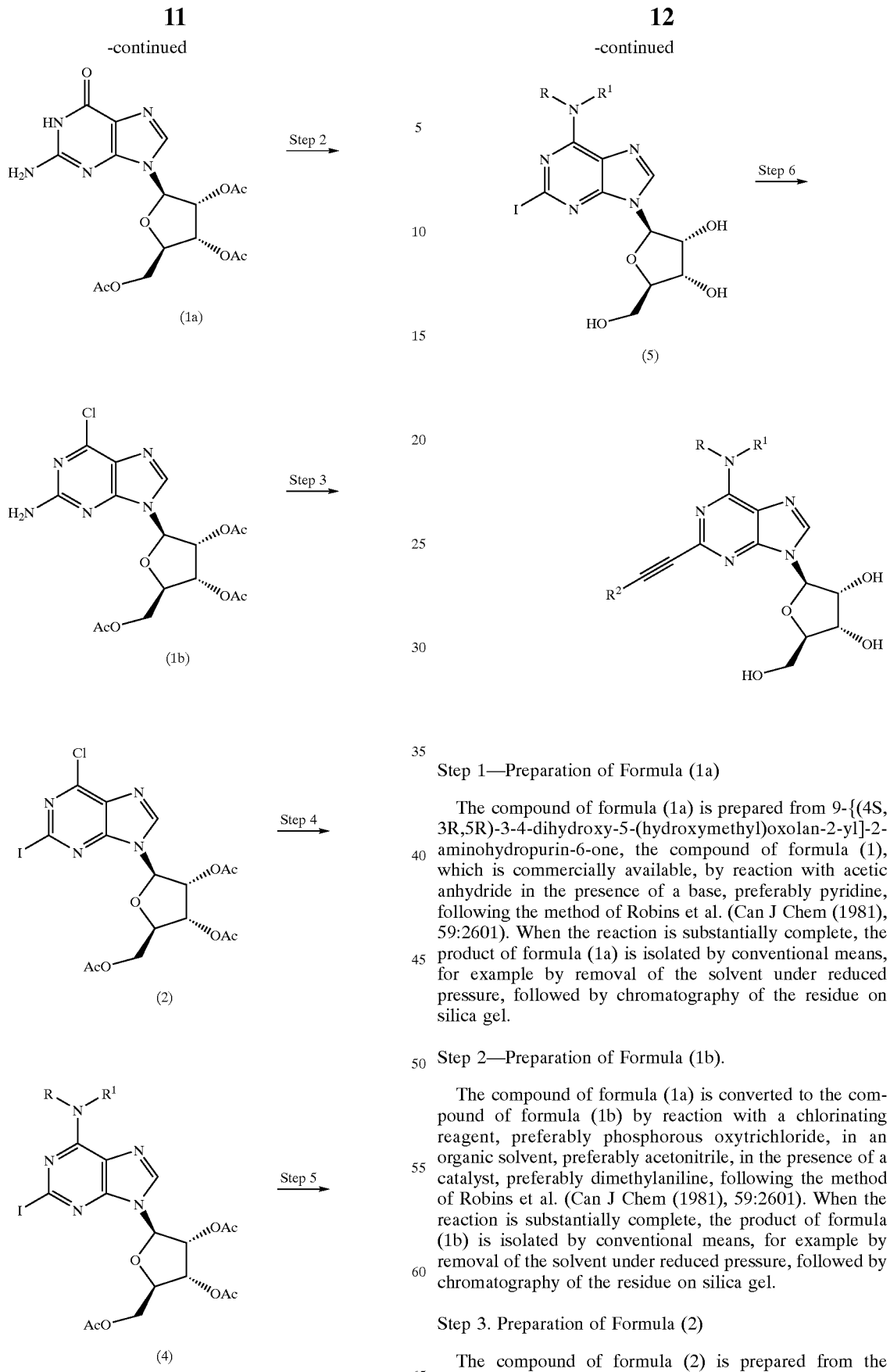

Step 1—Preparation of Formula (1a)

The compound of formula (1a) is prepared from 9-{[(4S, 3R,5R)-3-4-dihydroxy-5-(hydroxymethyl)oxolan-2-yl]-2-aminohydropurin-6-one, the compound of formula (1), which is commercially available, by reaction with acetic anhydride in the presence of a base, preferably pyridine, following the method of Robins et al. (Can J Chem (1981), 59:2601). When the reaction is substantially complete, the product of formula (1a) is isolated by conventional means, for example by removal of the solvent under reduced pressure, followed by chromatography of the residue on silica gel.

Step 2—Preparation of Formula (1b).

The compound of formula (1a) is converted to the compound of formula (1b) by reaction with a chlorinating reagent, preferably phosphorous oxytrichloride, in an organic solvent, preferably acetonitrile, in the presence of a catalyst, preferably dimethylaniline, following the method of Robins et al. (Can J Chem (1981), 59:2601). When the reaction is substantially complete, the product of formula (1b) is isolated by conventional means, for example by removal of the solvent under reduced pressure, followed by chromatography of the residue on silica gel.

Step 3. Preparation of Formula (2)

The compound of formula (2) is prepared from the compound of formula (1b) by diazotisation/iodination (Nair, V., et al. 1988. J. Org. Chem, 53:3051), by reacting with an alkyl nitrite, preferably pentyl nitrite, in the presence of an iodide source, preferably diiodomethane. When the reaction is substantially complete, the product of formula (2) is isolated by conventional means, for example by removal of the solvent under reduced pressure, followed by chromatography of the residue on silica gel.

Step 4—Preparation of Formula (4)

The compound of formula (2) is then converted to a compound of formula (4) by reaction with a compound of formula $RR^1NH$ (3), which may be obtained commercially, or prepared by means well known in the art. The reaction is conducted in an inert solvent, for example tetrahydrofuran, at about room temperature for about 68–128 hours, preferably about 96 hours. When the reaction is substantially complete, the product of formula (3) is isolated by conventional means, for example by removal of the solvent in vacuo followed by chromatography of the residue on silica gel.

Step 5—Preparation of Formula (5).

The compound of formula (4) is then converted to a compound of formula (5) by reaction with methanolic ammonia at room temperature for about 2–10 days, preferably about 4 days. When the reaction is substantially complete, the product of formula (5) is isolated by conventional means, for example by removal of solvent under reduced pressure followed by chromatography of the residue on silica gel.

Step 6. Preparation of Formula I.

The compound of formula (5) is then converted to a compound of Formula I by reaction with an acetylene derivative of formula $R^2$—C≡CH, in a polar solvent, preferably dimethylformamide, in the presence of a tertiary base, preferably triethylamine, and a copper salt, for example CuI, and a catalyst, preferably, dichlorobis(triphenylphosphine) palladium (II). The reaction mixture is stirred at room temperature for about 1–10 hours. When the reaction is substantially complete, the product of Formula I is isolated by conventional means, for example by removal of solvent under reduced pressure followed by chromatography of the residue on silica gel.

Preparation of Formula (I) where $R^3$ is $R^4R^5N(O)C$—.

Preparation of the compounds of Formula I where $R^3$ is $R^4R^5N(O)C$— is shown in Reaction Scheme II.

REACTION SCHEME II

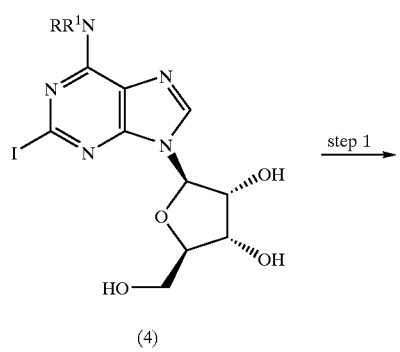

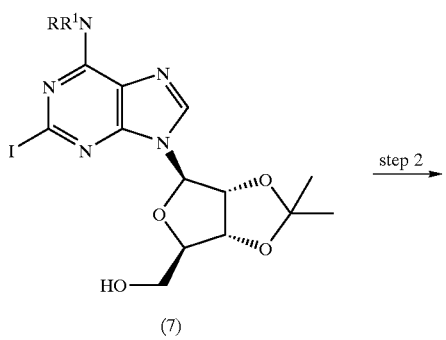

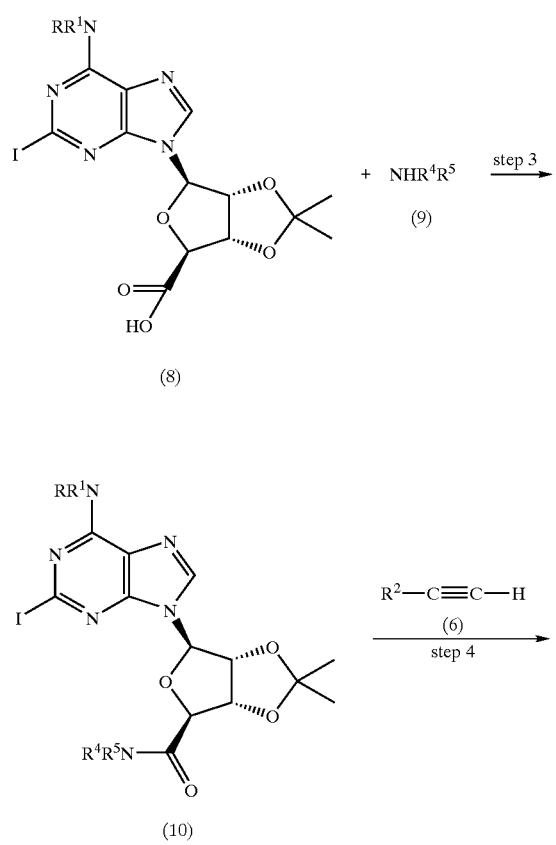

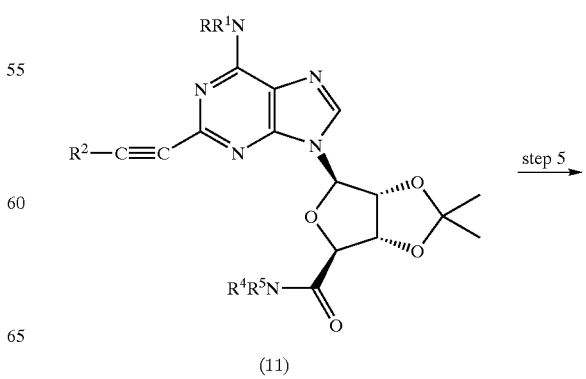

-continued

Formula I

Step 1—Preparation of Formula (7).

The compound of formula (7) is prepared conventionally from the compound of formula (5), by reaction with 2,2-dimethoxypropane in an inert solvent, preferably dimethylformamide, in the presence of an acid catalyst, preferably p-toluenesulfonic acid, at a temperature of about 40–90° C., preferably about 70° C., for about 24–72 hours, preferably about 48 hours. When the reaction is substantially complete, the product of formula (7) is isolated by conventional means, for example removal of the solvent under reduced pressure and purifying the residue by flash chromatography.

Step 2—Preparation of Formula (8)

The compound of formula (7) is then converted to a compound of formula (8) by dissolving in an inert solvent, preferably dry N,N-dimethylformamide and reacting with an oxidizing agent, preferably pyridinium dichromate. Preferably, the reaction is conducted in the dark at room temperature for about 15–48 hours, preferably about 30 hours. When the reaction is substantially complete, the product of formula (8) is isolated by conventional means, for example by filtering and purifying the residue by flash chromatography.

Step 3—Preparation of Formula (10)

The compound of formula (8) is converted to a compound of formula (10) by reaction with a compound of formula $R^4R^5NH$ (9). Briefly, a compound of formula (8) is reacted with a compound of formula (9) in the presence of a dehydrating agent, preferably dicyclohexylcarbodiimide, in an inert solvent, for example an alcohol, preferably as described in Advanced Organic Chemistry (1992. March, J. John Wiley and Sons p.395). When the reaction is substantially complete, the product of formula (10) is isolated by conventional means, for example by removal of the solvent under reduced pressure, followed by chromatography of the residue on silica gel.

Step 4—Preparation of Formula (11).

The compound of formula (10) is then converted to a compound of formula (11) by reaction with the appropriate acetylene derivative of formula $R^2$—C≡CH, in the presence of a tertiary base, preferably triethylamine, and a copper salt, for example CuI, and a catalyst, preferably dichlorobis(triphenylphosphine)palladium (II). The reaction mixture is stirred at room temperature for about 5 to 48 hours. When the reaction is substantially complete, the product of formula (11) is isolated by conventional means, for example by removal of solvent under reduced pressure followed by chromatography of the residue on silica gel.

Step 5. Preparation of Formula (I).

The compound of formula (11) is then deprotected by treatment with an acid, preferably an organic acid, for example acetic acid. The reaction is carried out in a mixture of the acid and water, at about 50–100° C., preferably about 80–90° C., for about 10–48 hours, preferably about 16 hours. When the reaction is substantially complete, the product of Formula I is isolated by conventional means, for example by removal of the solvent under reduced pressure, followed by chromatography of the residue on silica gel.

Preparation of Compounds of Formula (6)

All compounds of the formula (6) are commercially available or may be prepared by means well known in the art. For example, 4-ethynyl-1-phenylacetonitrile and 1-acetyl-4-ethynylbenzene, which were synthesized following the procedure of Takahashi et al. (Synthesis 1980,8, 627–630) as shown in Reaction Scheme III.

REACTION SCHEME III

Step 1—Preparation of Formula (13).

The compound of formula (12) is reacted with 2,2-dimethyl-2-silabut-3-yne, both of which are commercially available, in the presence of a tertiary base, preferably triethylamine, in the presence of CuI, and a catalyst, preferably dichlorobis(triphenylphosphine)palladium (II). The reaction is carried out for about 0.5–72 hours, preferably about 24 hours. When the reaction is substantially complete, the compound of formula (14) is isolated by conventional means, for example by removing the solvent in vacuo followed by chromatography of the residue.

Step 2—Preparation of Formula (6).

The compound of formula (6) is obtained from the compound of formula (12) by treatment with a base, preferably sodium hydroxide, in an alcohol, preferably methanol, at about room temperature for about 0.5 minutes-10 hours, preferably about 1 hour. When the reaction is substantially complete the compound of formula (6) is isolated by conventional means, for example by chromatography.

Utility, Testing and Administration

General Utility

The compounds of Formula I are effective in the treatment of conditions known to respond to administration of $A_3$ adenosine receptor agonists. Such conditions include, but are not limited to, modulation of cell proliferation processes. In particular, compounds that are $A_3$ adenosine receptor agonists have utility in the therapeutic and/or prophylactic treatment of cancer, cardiac disease, infertility, kidney disease, inflammation, cardiac and neurological ischemia, and CNS disorders. Additionally, they are useful for countering the toxic side effect of chemotherapeutic drugs, such as leukopenia and neutropenia.

Testing

Activity testing is conducted as described in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17$^{th}$ Ed. (1985) and "Modem Pharmaceutics", Marcel Dekker, Inc. 3$^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and is generally administered in a pharmaceutically effective amount. Preferably, for oral administration, each dosage unit contains from 10 mg to 2 g of a compound of Formula I, more preferably from 10 to 700 mg, and for parenteral administration, preferably from 10 to 700 mg of a compound of Formula I, more preferably about 50–200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of the Compound of Formula (1a).

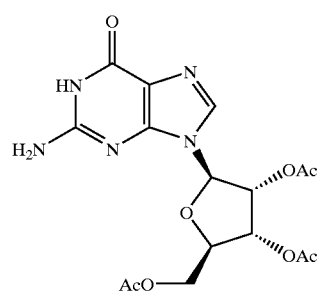

(1a)

The compound of formula (1), guanosine, was converted to the compound of formula (1a), (2R,3R,4R,5R)-4-acetyloxy-5-(acetyloxymethyl)-2-(2-amino-6-oxohydropurin-9-yl)oxolan-3-yl acetate, by the method of Robins et al. (Can J Chem (1981).59:2601), as follows.

Guanosine was dissolved in dry pyridine and N,N-dimethylformamide and acetic anhydride was added. The mixture was heated at 75° C. for 4 hours, filtered while hot, then the solvent was removed under reduced pressure. The residue was washed with isopropanol and dried to provide crude (2R,3R,4R,5R)-4-acetyloxy-5-(acetyloxymethyl)-2-(2-amino-6-oxohydropurin-9-yl)oxolan-3-yl acetate, which can be used in the next step with no further purification, or purified by recrystallization from isopropanol.

EXAMPLE 2

Preparation of the Compound of Formula (1b).

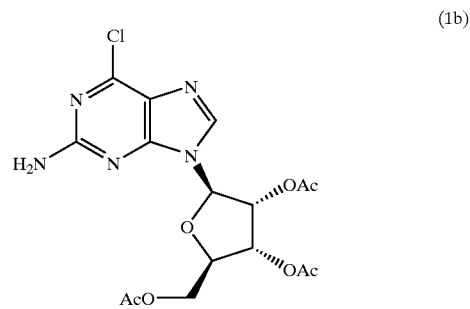

(1b)

The compound of formula (1a) was converted to the compound of formula (1b), (2R,3R,4R,5R)-4-acetyloxy-5-(acetyloxymethyl)-2-(2-amino-6-chloropurin-9-yl)oxolan-3-yl acetate following the method of Robins et al. (Can J Chem (1981).59:2601), as follows.

To a mixture of (2R,3R,4R,5R)-4-acetyloxy-5-(acetyloxymethyl)-2-(2-amino-6-oxohydropurin-9-yl) oxolan-3-yl acetate and tetraethylammonium chloride in acetonitrile was added N,N-dimethylaniline and phosphoryl chloride at room temperature. The mixture was heated at reflux for 10 minutes, then solvent removed under reduced pressure. The residue was dissolved in chloroform, stirred with ice, then washed with water, sodium bicarbonate solution, water, dried over magnesium sulfate, and filtered. Isopropanol was added to the filtrate, which was reduced in volume under reduced pressure. The crystalline product that separated was filtered off, washed with isopropanol, and dried under reduced pressure, to provide (2R,3R,4R,5R)-4-acetyloxy-5-(acetyloxymethyl)-2-(2-amino-6-chloropurin-9-yl)oxolan-3-yl acetate.

EXAMPLE 3

Preparation of the Compound of the Formula (2).

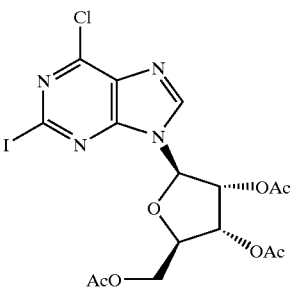

(2)

The compound of formula (1b) was converted into the compound of formula (2), (2R,3R,4R,5R)-4-acetyloxy-5-(acetyloxymethyl)-2-(6-chloro-2-iodopurin-9-yl)oxolan-3-yl acetate, by following the method of Nair et al. (1988, J. Org. Chem. 53:3051), as follows.

To a solution of (2R,3R,4R,5R)-4-acetyloxy-5-(acetyloxymethyl)-2-(2-amino-6-chloropurin-9-yl)oxolan-3-yl acetate in acetonitrile was added diiodomethane and n-pentyl nitrite. The mixture was heated under nitrogen for 20 hours, then solvent removed under reduced pressure. The residue was purified by chromatography on silica gel, eluting with hexanes to hexanes/ethyl acetate 2:1, to provide (2R,3R,4R,5R)-4-acetyloxy-5-(acetyloxymethyl)-2-(6-chloro-2-iodopurin-9-yl)oxolan-3-yl acetate, which may be recrystallized from ethanol.

EXAMPLE 4

Preparation of a Compound of Formula (4)

A. Preparation of a Compound of Formula (4) where R is Hydrogen and $R^1$ is Methoxy.

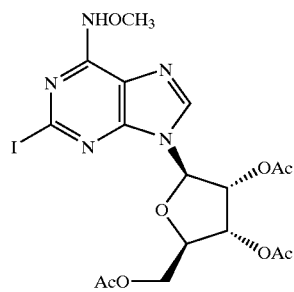

(4)

(2R,3R,4R,5R)-4-acetyloxy-5-(acetyloxymethyl)-2-(6-chloro-2-iodopurin-9-yl)oxolan-3-yl acetate (3.71 mmol) in dry tetrahydrofuran (60ml) was mixed with O-methyl hydroxylamine hydrochloride (37.1 mmol) and triethylamine (6.2 mL). The mixture was stirred at room temperature for 96 hours under an atmosphere of nitrogen. The solvent was removed in vacuo and the residue chromatographed on a flash silica gel column eluting with $CHCl_3$—$CH_3OH$ (99:1), to give (2R,3R,4R,5R)-4-acetyloxy-5-(acetyloxymethyl)-2-[2-iodo-6-(methoxyamino)purin-9-yl]oxolan-3-yl acetate, a compound of formula (4), which was crystallized from a mixture of chloroform/hexanes (1:1).

B. Preparation of Compounds of Formula (4) varying $R^1$

Similarly, following the procedure of 4A above, but replacing O-methylhydroxylamine hydrochloride with O-ethylhydroxylamine hydrochloride, O-propylamine hydrochloride, and O-cyclopropylhydroxylamine hydrochloride, the following compounds of formula (4) are prepared:

(2R,3R,4R,5R)-4-acetyloxy-5-(acetyloxymethyl)-2-[2-iodo-6-(ethoxyamino)purin-9-yl]oxolan-3-yl acetate;
(2R,3R,4R,5R)-4-acetyloxy-5-(acetyloxymethyl)-2-[2-iodo-6-(propoxyamino)purin-9-yl]oxolan-3-yl acetate; and
(2R,3R,4R,5R)-4-acetyloxy-5-(acetyloxymethyl)-2-[2-iodo-6-(cyclopropoxyamino)purin-9-yl]oxolan-3-yl acetate.

C. Preparation of Compounds of Formula (4) Varying $R^1$

Similarly, following the procedure of 4A above, but replacing O-methylhydroxylamine hydrochloride with other hydroxylamine derivatives, other compounds of formula (4) are prepared.

EXAMPLE 5

Preparation of a Compound of Formula (5)

A. Preparation of a Compound of Formula (5) where R is Hydrogen and $R^1$ is Methoxy.

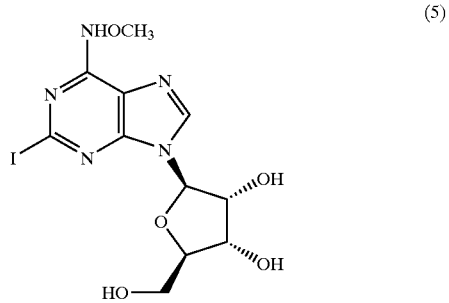

(5)

Methanolic ammonia (30 mL) was added to (2R,3R,4R,5R)-4-acetyloxy-5-(acetyloxymethyl)-2-[2-iodo-6-(methoxyamino)purin-9-yl]oxolan-3-yl acetate (3.03 mmol). The mixture was allowed to stand at room temperature for 96 hours, then solvent was removed in vacuo and the residue chromatographed on a flash silica gel column eluting with $CHCl_3$—$CH_3OH$ (97:3) to give the compound of formula (5), (4S,2R,3R,5R)-5-(hydroxymethyl)-2-[2-iodo-6-(methoxyamino)purin-9-yl]oxolane-3,4-diol, which was crystallized from acetonitrile,.

B. Preparation of Compounds of Formula (5) Varying $R^1$

Similarly, following the procedure of 5A above, but replacing (2R,3R,4R,5R)-4-acetyloxy-5-(acetyloxymethyl)-2-[2-iodo-6-(methoxyamino)purin-9-yl]oxolan-3-yl acetate with other compounds of formula (4),, the following compounds of formula (5) are prepared:

(4S,2R,3R,5R)-5-(hydroxymethyl)-2-[2-iodo-6-(ethoxyamino)purin-9-yl]oxolane-3,4-diol;
(4S,2R,3R,5R)-5-(hydroxymethyl)-2-[2-iodo-6-(methoxyamino)purin-9-yl]oxolane-3,4-diol; and
(4S,2R,3R,4R)-5-(hydroxymethyl)-2-[2-iodo-6-(cyclopropoxyamino)purin-9-yl]oxolane-3,4-diol.

C. Preparation of Compounds of Formula (5) Varying $R^1$

Similarly, following the procedure of 5A above, but replacing (2R,3R,4R,5R)-4-acetyloxy-5-(acetyloxymethyl)-2-[2-iodo-6-(methoxyamino)purin-9-yl]oxolan-3-yl acetate with other compounds of formula (4), other compounds of formula (5) are prepared:

EXAMPLE 6

Preparation of a Compound of Formula I

A. Preparation of a Compound of Formula I where R is Hydrogen, $R^1$ is Methoxy $R^2$ is Phenyl and $R^3$ is Hydroxymethyl

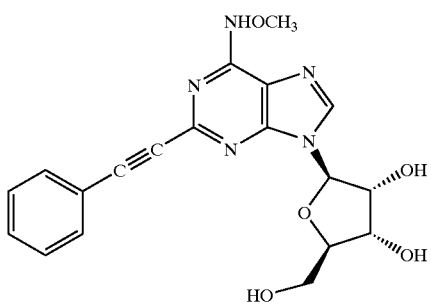

Formula I

CuI (0.35 mg, 0.002 mmol) and phenylacetylene (2.1 mmol) were added to a solution of (4S,2R,3R,5R)-5-(hydroxymethyl)-2-[2-iodo-6-(methoxyamino)purin-9-yl]oxolane-3,4-diol (0.35 mmol), a compound of formula (5), in dry N,N-dimethylformamide (6 mL) and triethylamine (1.4 mL) under an atmosphere of nitrogen in the presence of bis(triphenylphosphine)palladium dichloride (5 mg, 0.007 mmol). The reaction mixture was stirred at room temperature for 5 hours. After evaporation under reduced pressure the residual oil was purified by silica gel column chromatography, eluting with chloroform/methanol 90/10. After evaporation in vacuo, the residual oil was purified by silica gel column chromatography, eluting with the suitable mixture of solvents, to provide (4S,2R,3R,5R)-5-(hydroxymethyl)-2-[6-(methoxyamino)-2-(2-phenylethynyl)purin-9-yl]oxolane-3,4-diol, a compound of Formula I (mp 175–177° C.).

$^1$H NMR (DMSO-d6) d 3.65 (m, 2H, CH2-5$^1$), 3.81 (s, 3H, OCH3), 3.99 (m, 1H, H-4$^1$), 4.16 (m, 1H, H-3$^1$), 4.57 (m, 1H, H-2$^1$), 5.97 (d, 1H, J=5.9 Hz, H-1$^1$), 7.50 (m, H-Ph), 7.68 (m, 2H, H-Ph), 8.58 (s, 1H, H-8), 11.26 (s, 1H, NH).

B. Preparation of a Compound of Formula I where R is Hydrogen R$^1$ is Methoxy, and R$^3$ is Hydroxymethyl, varying R$^2$ Similarly, following the procedure of 6A above, but replacing phenylacetylene with other compounds of formula R$^2$—C≡CH, the following compounds of formula (6) were prepared:

(4S,2R,3R,5R)-5-(hydroxymethyl)-2-[6-(methoxyamino)-2-[(2-(4-methylphenyl)ethynyl]-purin-9-yl]oxolane-3,4-diol; mp 187–189° C.;

(4S,2R,3R,5R)-2-{2-[2-(4-fluorophenyl)ethynyl}-6-(methoxyamino)purin-9-yl}-5-(hydroxymethyl)oxolane-3,4-diol; mp 209–211° C.;

(4S,2R,3R,5R)-5-hydroxymethyl)-2-{6-(methoxyamino-2-[2-(4-pentylphenylethynyl)]purin-9-yl}oxolane-3,4-diol; mp 105–107° C.;

(4S,2R,3R,5R)-2-[-2-(4-hydroxypent-1-ynyl)-6-(methoxyamino) purin-9-yl}-5-(hydroxymethyl)oxolane-3,4-diol.

(4S,2R,3R,5R)-5-(hydroxymethyl)-2-[6-(methoxyamino)2-[(2-(3-trifluoromethylphenyl))-ethynyl]purin-9-yl] oxolane-3,4-diol; mp 110–112° C.;

(4S,2R,3R,5R)-5-(hydroxymethyl)-2-[6-(methoxyamino)-2-[(2(4-methoxyphenyl)ethynyl]-purin-9-yl]oxolane-3,4-diol; mp 110–112° C.; (4S,2R,3R,5R)-2-{2-[2-hex-1-ynyl-6-methoxyamino)purin-9-yl}-5-diol; mp 83–85° C.;

(4S,2R,3R,5R)-2-{2-[(3,3-dimethyl-3-silabut-1-ynyl)-6-(methoxyamino)purin-9-}-5-(hydroxymethyl)oxolane-3, 4-diol; mp 100–102° C. (dec);

4-(2-{9-[(4S,2R,3R,5R-3,4-dihydroxy-5-(hydroxymethyl) oxolan-2-yl]-6-(methyoxyamino)-purin-2-yl]ethynylbenzamide; mp >250° C.;

(4S,2R,3R,5R)-2-{ 1-[1-hydroxycyclohexyl)ethynyl]-6-(methoxyamino)purin-9-yl}-5-(hydroxymethyl)oxolane-3,4-diol; mp 120–122° C. (dec);

(4S,2R,3R,5R)-5-(hydroxymethyl)-2-[6-(methoxyamino)-2-[(2-(2-pyridyl)ethynyl)purin-9-yl]oxolane-3,4-diol; mp 150–152° C.;

(4S,2R,3R,5R)-5-(hydroxymethyl)-2-[6-(methoxyamino)-2-[(2-(3-pyridyl)ethynyl)purine-9-yl]oxolane-3,4-diol; mp 164–168° C. (dec);

(4S,2R,3R,5R)-5-(hydroxymethyl)-2-[6-(methoxyamino)-2-[(2-(4-pyridyl)ethynyl)purine-9-yl]oxolane-3,4-diol; mp 205° C. (dec);

1-[4-(2-{9-[4S,2R,3R,5R]-3,4-dihydroxy-5-(hydroxymethyl)oxolan-2-yl]-6-(methoxyamino)-purin-2-yl}ethynyl)phenyl]ethan-1-one; mp 217–219° C.;

2-[4-(2-{9-[4S,2R,3R,5R)-3,4-dihydroxy-5-(hydroxymethyl)oxolan-2-yl]-6-(methyosyamino)-purin-2-yl}ethynyl)phenyl]ethanenitrile; mp 120–122° C. (dec);

(4S,2R,3R,5R)-2[ethynyl-6-(methoxyamino)purin-9-yl]-5-(hydroxymethyl)oxolane-3,4-diol; and 6-{(4S,2R,3R,5R)-3,4-dihydroxy-5-(hydroxymethyl)oxolan-2-yl]-6-(methoxyamino)purin-2-yl}ethynyl)hex-5-ynenitrile. mp 165–167° C.

NMR spectra were obtained for all of the above compounds of Formula I, and found to be satisfactory. For example:

(4S,2R,3R,5R)-2-{2-[2-hex-1-ynyl-6-methoxyamino)purin-9-yl}-5-(hydroxymethyl)oxolane-3,4-diol; $^1$H NMR (DMSO-d6) d 0.93 (t, 3H, J=7.0 Hz, CH3), 1.53 (m, 4H, (CH2)2CH3), 2.45 (m, 2H, CH2C†C), 3.62 (m, 2H, CH2-5$^1$), 3.77 (s, 3H, OCH3), 3.96 (m, 1H, H-4$^1$), 4.14 (m, 1H, H-31), 4.53 (m, 1H, H-2$^1$), 5.91 (d, 1H, J=5.9 Hz, H-1$^1$), 8.52 (s, 1H, H-8), 11.11 (s, 1H, NH).

(4S,2R,3R,5R)-5-(hydroxymethyl)-2-[6-(methoxyamino)-2-[(2-(4-methylphenyl)ethynyl]-purin-9-yl]oxolane-3,4-diol; $^1$H NMR (DMSO-d6) d 2.38 (s, 3H, CH3-Ph), 3.65 (m, 2H, CH2-5$^1$), 3.81 (s, 3H, OCH3), 3.99 (m, 1H, H-4$^1$), 4.16 (m, 1H, H-3$^1$), 4.56 (m, 1H, H-2$^1$), 5,96 (d, 1H, J=5.1 Hz, H-1$^1$), 7.30 (d, 2H, J=7.7 Hz, H-Ph), 7.55 (d, 2H, J=7.7 Hz, H-Ph), 8.57 (s, 1H, H-8), 11.23 (s, 1H, NH).

(4S,2R,3R,5R)-2-{2-[2-(4-fluorophenyl)ethynyl}-6-(methoxyamino)purin-9-yl}-5-(hydroxymethyl)oxolane-3,4-diol; $^1$H NMR (DMSO-d6) d 3.65 (m, 2H, CH2-5$^1$), 3.81 (s, 3H, OCH3), 3.98 (m, 1H, H-4$^1$), 4.16 (m, 1H, H-3$^1$), 4.56 (m, 1H, H-2$^1$), 5.96 (d, 1H, H=5.6 Hz, H-1$^1$), 7.34 (m, 2H, H-Ph), 7.74 (m, 2H, H-Ph), 8.58 (s, 1H, H-8), 11.26 (s, 1H, NH)

C. Preparation of a Compound of Formula I Varying R, R$^1$, R$^2$, and R$^3$ is Hydroxymethyl Similarly, following the procedure of 6A above, but optionally replacing (4S,2R,3R,5R)-5-(hydroxymethyl)-2-[2-iodo-6-(methoxyamino)purin-9-y]oxolane-3,4-diol with other compounds of formula (5), and optionally replacing phenylacetylene with other compounds of formula R$^2$—C≡CH, the following compounds of Formula I are prepared:

(4S,2R,3R,5R)-5-(hydroxymethyl)-2-[6-(methoxymethylamino)-2-(2-phenylethynyl)purin-9-yl] oxolane-3,4-diol;

(4S,2R,3R,5R)-5-(hydroxymethyl)-2-[6-(ethoxyamino)-2-(2-phenylethynyl)purin-9-yl]oxolane-3,4-diol;

(4S,2R,3R,5R)-5-(hydroxymethyl)-2-[6-(propoxyamino)-2-(2-phenylethynyl)purin-9-yl]oxolane-3,4-diol;

(4S,2R,3R,5R)-5-(hydroxymethyl)-2-[6-(cyclopropoxyamino)-2-(2-phenylethynyl)purin-9-yl]oxolane-3,4-diol;
(4S,2R,3R,5R)-5-(hydroxymethyl)-2-[6-(ethoxyamino)-2-[(2-(4-methylphenyl)ethynyl]-purin-9-yl]oxolane-3,4-diol;
(4S,2R,3R,5R)-2-{2-[2-(4-fluorophenyl)ethynyl}-6-(propoxyamino)purin-9-yl}-5-(hydroxymethyl)oxolane-3,4-diol;
(4S,2R,3R,5R)-5-hydroxymethyl)-2-{6-(cyclopropoxyamino2-[2-(4-pentylphenylethynyl)]purin-9-yl}oxolane-3,4-diol;
(2S,3S,4R,5R)-3,4-dihydroxy-5-[2-(4-hydroxypent-1-ynyl)-6-(ethoxyamino)purin-9-yl]oxolane-3,4-diol;
(4S,2R,3R,5R)-5-(hydroxymethyl)-2-[6-(propoxyamino)2-[(2(3-trifluoromethylphenyl))-ethynyl]purin-9-yl]oxolane-3,4-diol;
(4S,2R,3R,5R)-5-(hydroxymethyl)-2-[6-(cyclopropoxyamino)-2-[(2(4-methoxyphenyl)ethynyl]-purin-9-yl]oxolane-3,4-diol;
(4S,2R,3R,5R)-2-{2-[2-hex-1-ynyl-6-ethoxyamino)purin-9-yl}-5-hydroxymethyl)oxolane-3,4-diol;
(4S,2R,3R,5R)-2-{1-[1-hydroxycyclohexyl)ethynyl]-6-(propoxyamino)purin-9-yl}-5-(hydroxymethyl)oxolane-3,4-diol; and
(4S,2R,3R,5R)-5-(hydroxymethyl)-2-[6-(cyclopropoxyamino)-2-[(2-(2-pyridyl)ethynyl)purin-9-yl]oxolane-3,4-diol.

EXAMPLE 7
Preparation of a Compound of Formula I
A. Preparation of a Compound of Formula I where R is Hydrogen, $R^1$ is Methoxy, $R^3$ is $R^4R^5NC(O)$—, in which $R^4$ is Hydrogen and $R^5$ is Methyl or Ethyl, Varying $R^2$ Using the methods illustrated in Reaction Scheme II, the following compounds of Formula I where $R^3$ is $R^4R^5NC(O)$— in which $R^4$ is hydrogen and $R^5$ is methyl or ethyl were made.

{(2S,3S,4R,5R)-3,4-dihydroxy-5-[6-(methoxyamino)-2-(2-(2-pyridyl)ethynyl)purin-9-yl]oxolan-2-yl}-N-methylcarboxamide; mp 163–166° C. (dec);
{(2S,3S,4R,5R)-3,4-dihydroxy-5-[6-(methoxyamino)-2-(2-(2-pyridyl)ethynyl)purin-9-yl]oxolan-2-yl}-N-ethylcarboxamide; mp 205° C. (dec);
{(2S,3S,4R,5R)-3,4-dihydroxy-5-{6-(methoxyamino)-2-[2-(4-methylphenyl)ethynyl]purin-9-yl}oxolan-2-yl)-N-methylcarboxamide; mp 160–163° C.;
{(2S,3S,4R,5R)-3,4-dihydroxy-5-{6-(methoxyamino)-2-[2-(4-methylphenyl)ethynyl]purin-9-yl}oxolan-2-yl)-N-ethylcarboxamide; mp 164–168° C.;
{(2S,3S,4R,5R)-3,4-dihydroxy-5-{6-(methoxyamino)-2-[2-phenylethynyl]purin-9-yl}oxolan-2-yl)-N-methylcarboxamide; mp 164–167° C. (dec);
{(2S,3S,4R,5R)-3,4-dihydroxy-5-{6-(methoxyamino)-2-[2-phenylethynyl]purin-9-yl}oxolan-2-yl)-N-ethylcarboxamide; mp 186–189° C. (dec);
{(2S,3S,4R,5R)-{2-[2-(4-fluorophenyl)ethynyl]-6-(methoxyamino)purin-9-yl}-3,4-dihydroxyoxolan-2-yl)-N-methylcarboxamide; mp 166–169° C.;
{(2S,3S,4R,5R)-{2-[2-(4-fluorophenyl)ethynyl]-6-(methoxyamino)purin-9-yl -3,4-dihydroxyoxolan-2-yl)-N-ethylcarboxamide; mp 160–163° C.;
{(2S,3S,4R,5R)-3,4-dihydroxy-5-{6-(methoxyamino)-2-[2-(4-pentylphenyl)ethynyl]purin-9-yl}oxolan-2-yl)-N-methylcarboxamide; mp 154–156° C.;
{(2S,3S,4R,5R)-3,4-dihydroxy-5-{6-(methoxyamino)-2-[2-(4-pentylphenyl)ethynyl]purin-9-yl}oxolan-2-yl)-N-ethylcarboxamide; mp 153–157° C.;
1-[4-(2-{9-[4S,2R,3R,5R]-3,4-dihydroxy-5-(hydroxymethyl)oxolan-2-yl]-6-methoxyamino)-purin-2-yl}ethynyl)phenyl]ethan-1-one-N-methylcarboxamide. mp 127–129° C. (dec); and
1-[4-(2-{9-[4S,2R,3R,5R]-3,4-dihydroxy-5-(hydroxymethyl)oxolan-2-yl]-6-(methyoxyamino)-purin-2-yl}ethynyl)phenyl]ethan-1-one-N-ethylcarboxamide. mp 160–164° C.

$^1$H NMR spectra were obtained for all of the above compounds of Formula I, and found to be satisfactory. For example:

{(2S,3S,4R,5R)-{2-[2-(4-fluorophenyl)ethynyl]-6-(methoxyamino)purin-9-yl}-3,4-dihydroxyoxolan-2-yl)-N-ethylcarboxamide;$^1$H NMR (DMSO-$d_6$) δ 1.02 (t, 3H, J=7.2 Hz, CH$_2$CH$_3$), 3.24 (m, 2H, CH$_2$CH$_3$), 3.80 (s, 3H, OCH$_3$), 4.17 (m, 1H, H-3'), 4.33 (d, 1H, H=1.6 Hz, H-4'), 4.61 (m, 1H, H-2'), 5.62 (d, 1H, J=6.2 Hz, OH), 5.77 (d, 1H, J=4.4 Hz, OH), 6.00 (d, 1H, J=7.3 Hz, H-1'), 7.33 (m, 2H, H-Ph), 7.71 (m, 2H, H-Ph ), 8.44 (m, 1H, NHCH$_2$), 8.62 (s, 1H, H-8 ), 11.27 (bs, 1H, NHOCH$_3$).
{(2S,3 S,4R,5R)-3,4-dihydroxy-5-{6-(methoxyamino)-2-[2-phenylethynyl]purin-9-yl}oxolan-2-yl)-N-ethylcarboxamide; $^1$H NMR (DMSO-$d_6$) δ 1.03 (t, 3H, J=7.2 Hz, CH$_2$CH$_3$), 3.22 (m, 2H, CH$_2$CH$_3$), 3.81 (s, 3H, OCH$_3$), 4.15 (bs, 1H, H-3'), 4.34 (s, 1H, H-4'), 4.65 (m, 1H, H-2'), 5.61 (d, 1H, J=6.6 Hz, OH), 5.76 (d, 1H, J=4.4 Hz, OH), 6.10 (d, 1H, J=7.3 Hz, H-1'), 7,49 (m, 3H, H-Ph), 7.64 (m, 2H, H-Ph), 8.49 (t, 1H, J=4.0 Hz, NHCH$_2$), 8.63 (s, 1H, H-8), 11.32 (bs, 1H, NHOCH$_3$).
{(2S,3S,4R,5R)-3,4-dihydroxy-5-{6-(methoxyamino)-2-[2-(4-methylphenyl)ethynyl]purin-9-yl}oxolan-2-yl)-N-ethylcarboxamide; $^1$H NMR (DMSO-$d_6$) δ 1.02 (t, 3H, J=7.2 Hz, CH$_2$CH$_3$), 2.36 (s, 3H, CH$_3$Ph), 3.32 (m, 2H, CH$_2$CH$_3$), 3.79 (s, 3H, OCH$_3$), 4.16 (m, 1H, H-3'), 4.32 (m, 1H, H-4'), 4.61 (m, 1H, H-2'), 5.61 (d, 1H, J=6.2 Hz, OH), 5.76 (d, 1H, J=4.0 Hz, OH), 6.01 (d, 1H, J=7.0 Hz, H-1'), 7.28 (m, 2H, H-Ph), 7.51 (m, 2H, H-Ph), 8.51 (m, 1H, NHCH$_2$), 8.60 (s, 1H, H-8), 11.31 (bs, 1H, NHOCH$_3$).

B. Preparation of a Compound of Formula I where R is Hydrogen, $R^1$ is Methoxy, and $R^3$ is $R^4R^5NC(O)$— where $R^4$ is Hydrogen and $R^5$ is Methyl or Ethyl, Varying $R^2$ Using the methods illustrated in Reaction Scheme II, the following compounds of Formula I where $R^3$ is $R^4R^5NC(O)$— in which $R^4$ is hydrogen and $R^5$ is methyl or ethyl are made:

{(2S,3S,4R,5R)-5-[2-ethynyl-6-(methoxyamino)purin-9-yl]-3,4-dihydroxyoxolan-2yl}-N-methylcarboxamide;
{(2S,3S,4R,5R)-3,4-dihydroxy-5-[6-(methoxyamino)-2-(2-phenylethynyl)purin-9-yl}oxolan-2-yl }-N-methylcarboxamide;
{(2S,3S,4R,5R)-3,4-dihydroxy-5-{6-(methoxyamino)-2-[2-(4-methylphenyl)ethynyl]purin-9-yl }oxolan-2-yl)-N-methylcarboxamide;
{(2S,3 S,4R,5R)-5-{2-[2-(4-acetylphenyl)ethynyl]-6-(methoxyamino)purin-9-yl}-3,4-dihydroxyoxolan-2-yl)-N-methylcarboxamide;
4-(2-{9{2S,3S,4R,5R)-5-(N-methylcarbamoyl)-3,4-dihydroxyoxolan-2-yl]-6-(methoxyamino)purin-2-yl}ethynyl)benzamide;
{(2S,3S,4R,5R)-3,4-dihydroxy-5-{2-[2-(2-hydroxycyclohexyl)ethynyl]-6-(methoxyamino)purin-9-yl}oxolan-2-yl)-N-methylcarboxamide;

{(2S,3S,4R,5R)-3,4-dihydroxy-5-[6-(methoxyamino)-2-(2-(2-pyridyl)ethynyl)purin-9-oxolan-2-yl}-N-methylcarboxamide;
[{2S,3 S,4R,5R)-5-(2-{2-[4-(cyanomethyl)phenyl]ethynyl}-6-(methoxyamino)purin-9-3,4-dihydroxyoxolan-2-yl]-N-methylcarboxamide;
(2S,3S,4R,5R)-3,4-dihydroxy-5-{6-(methoxyamino)-2-[2-(4-methoxyphenyl)ethynyl]purin-9-yl}oxolan-2-yl)-N-methylcarboxamide;
{(2S,3S,4R,5R)-3,4-dihydroxy-5-(6-(methoxyamino)-2-{2-[3-(trifluoromethyl)phenyl]ethynyl}purin-9-yl)oxolan-2-yl]-N-methylcarboxamide;
{(2S,3 S,4R,5R)-5-[2-hex-1-ynyl-6-(methoxyamino)purin-9-yl]-3,4-dihydroxyoxolan-2-}-N-methylcarboxamide;
{(2S,3S,4R,5R)-3,4-dihydroxy-5-[6-(methoxyamino)-2-(2-phenylethynyl)purin-9-yl]oxolan-2-yl}-N-ethylcarboxamide;
{(2S,3 S,4R,5R)-3,4-dihydroxy-5-[6-(ethoxyamino)-2-(2-phenylethynyl)purin-9-yl]oxolan-2-yl}-N-ethylcarboxamide;
{(2S,3S,4R,5R)-3,4-dihydroxy-5-[6-(propoxyamino)-2-(2-phenylethynyl)purin-9-yl]oxolan-2-yl }-N-ethylcarboxamide;
{(2S,3S,4R,5R)-3,4-dihydroxy-5-[6-(cyclopropoxyamino)-2-(2-phenylethynyl)purin-9-yl]oxolan-2-yl}-N-ethylcarboxamide; and
{(2S,3S,4R,5R)-3,4-dihydroxy-5-[6-(methoxyamino)-2-(2-phenylethynyl)purin-9-yl]oxolan-2-yl }-N-ethylcarboxamide.

The following examples illustrate the preparation of representative pharmaceutical formulations containing a compound of Formula I, such as those prepared in accordance with Example 6 and 7.

EXAMPLE 8

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

EXAMPLE 9

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 10

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

EXAMPLE 11

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 12

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 13

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |

-continued

| Ingredient | Amount |
| --- | --- |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 14

A subcutaneous formulation may be prepared as follows:

| Ingredient | Quantity |
| --- | --- |
| Active Ingredient | 5.0 mg |
| Corn Oil | 1.0 mL |

EXAMPLE 15

An injectable preparation is prepared having the following composition:

| Ingredients | Amount |
| --- | --- |
| Active ingredient | 2.0 mg/ml |
| Mannitol, USP | 50 mg/ml |
| Gluconic acid, USP | q.s. (pH 5–6) |
| water (distilled, sterile) | q.s. to 1.0 ml |
| Nitrogen Gas, NF | q.s. |

EXAMPLE 16

A topical preparation is prepared having the following composition:

| Ingredients | grams |
| --- | --- |
| Active ingredient | 0.2–10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C with stirring. A sufficient quantity of water at 60° C is then added with vigorous stirring to emulsify the ingredients, and water then added q.s. 100 g.

EXAMPLE 17
Sustained Release Composition

| Ingredient | Weight Range (%) | Preferred Range (%) | Most Preferred |
| --- | --- | --- | --- |
| Active ingredient | 50–95 | 70–90 | 75 |
| Microcrystalline cellulose (filler) | 1–35 | 5–15 | 10.6 |
| Methacrylic acid copolymer | 1–35 | 5–12.5 | 10.0 |
| Sodium hydroxide | 0.1–1.0 | 0.2–0.6 | 0.4 |
| Hydroxypropyl methylcellulose | 0.5–5.0 | 1–3 | 2.0 |
| Magnesium stearate | 0.5–5.0 | 1–3 | 2.0 |

The sustained release formulations of this invention are prepared as follows: compound and pH-dependent binder and any optional excipients are intimately mixed(dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl. methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400–600 mg, 650–850 mg, and 900–1100 mg. In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

Abbreviations

Gpp(NH)p: 5'-guanylyl-imididodiphosphate

R-PIA: phenylisopropyladenosine

TEM buffer: Buffer containing 50 mM Tris, 1 mM EDTA and 10 mM MgCl2

EXAMPLE 18

Stable transfection of HEK-293 or CHO cells. The cDNAs for human $A_1$, $A_{2A}$, $A_{2B}$ or $A_3$ AdoRs were prepared by RT-PCR from total RNA of human cells or tissues and sequenced on both strands. The expression vector containing each of these cDNAs and a second vector containing a neomycin or puromycin-resistance gene were introduced to HEK-293 or CHO cells by Lipofectin-Plus (Life Technology). Colonies were selected by growing transfected cells in the presence of neomycin or puromycin. Stably transfected cells were maintained in Dulbecco's modified Eagle's medium (DMEM) or F-12 medium with 10% fetal bovine serum, 100 μg/ml penicillin, 100 μg/ml streptomycin and appropriate concentrations of neomycin or puromycin. These stably transfected cells were referred to as HEK-"AdoR" or CHO-"AdoR" depending on the receptors that they express. For example, cells that were transfected with $A_3$ AdoRs were referred to as HEK-$A_3$ or CHO-$A_3$.

Membrane preparation. Monolayers of transfected cells were washed with phosphate buffered saline (PBS) and harvested in a buffer containing 10 mM HEPES (pH 7.4), 10 mM EDTA and protease inhibitors. The cells were homogenized in polytron for 1 minute at setting 4 and centrifuged at 29000 g for 15 minutes at 4° C. The cell pellets were washed with a buffer containing 10 mM HEPES (pH7.4), 1 mM EDTA and protease inhibitors, and were resuspended in the same buffer supplemented with 10% sucrose. Frozen aliquots were kept at −80° C.

Radioligand binding. The affinities of compounds for $A_1$, $A_{2A}$, $A_{2B}$ or $A_3$ AdoRs were determined in competition studies using radioligands such as $^3H$—CPX ($A_1$ antagonist), or $^3H$-CCPA ($A_1$ agonist), $^3H$-ZM214385 (A2A antagonist) or $^3H$-CGS21680 ($A_{2A}$ agonist), $^3H$-ZM214385 ($A_{2B}$ antagonist) or $^{125}I$-AB-MECA ($A_3$ agonist) and membranes of corresponding transfected cells. For example, to determine the affinity for $A_3$ AdoRs, the competition assays were started by mixing 0.2 nM $^{125}I$-AB-MECA with various concentrations of test compounds and 25 ug membrane proteins of HEK-$A_3$ or CHO-$A_3$ in TEM buffer (50 mM Tris, 1 mM EDTA and 10 mM $MgCl_2$) supplemented with 1 U/ml adenosine deaminase. The assays were incubated for 90 minutes, stopped by filtration onto GF/B filter plates using Packard Harvester and washed four times with ice-cold TM buffer (10 mM Tris, 1 mM MgCl2, pH 7.4). The amounts of radioligands that bound to the GF/B filter plates were determined by scintillation counting. Nonspecific binding was determined in the presence of 10 μM R—PIA or 1 μM IB-MECA. $B_{max}$ and $K_D$ values were calculated using GraphPad software.

The compounds of Formula were demonstrated to be $A_3$ adenosine receptor agonists in this assay. For example:

(4S,2R,3R,5R)-2-{2-[2-hex-1-ynyl-6-methoxyamino)purin-9-yl}-5-(hydroxymethyl)oxolane-3,4-diol; Ki(nM) 0.681;
(4S,2R,3R,5R)-5-(hydroxymethyl)-2-[6-(methoxyamino)-2-[(2-(4-methylphenyl)ethynyl]-purin-9-yl]oxolane-3,4-diol; Ki(nM) 0.331;
(4S,2R,3R,5R)-2-{2-[2-(4-fluorophenyl)ethynyl]-6-(methoxyamino)purin-9-yl}-5-(hydroxymethyl)oxolane-3,4-diol; Ki(nM) 0.422;
(4S,2R,3R,5R)-5-hydroxymethyl)-2-{6-(methoxyamino-2-[2-(4-pentylphenylethynyl)]purin-9-yl}oxolane-3,4-diol; Ki(nM) 0.388.

EXAMPLE 19
[$^{35}S$]GTPγS Binding Assays

The ability of the adenosine $A_3$-agonists to stimulate [35S] GTPγS binding is determined by a modification of the method described by Lorenzen et al. (1996 Mol. Pharmacol. 49:915). Briefly, membranes isolated from CHO cells (30–50 μg) are incubated in a volume of 0.1 ml containing 50 mM Tris-HCl buffer pH 7.4, 5 mM $MgCl_2$, 100 mM NaCl, 1 mM dithiothreitol, 0.2 units ml$^{-1}$ adenosine deaminase, 0.5% BSA, 1 mM EDTA, 10 mM GDP, and 0.3 nM [$^{35}S$]GTPγS. Various concentrations of PIA or the putative $A_3$ agonists are added and the cells incubated for 90 min at 30° C. Nonspecific binding is determined by the addition of 10 μM GTPγS to some of the membrane suspensions. At the end of the incubation, each suspension is filtered and the retained radioactivity determined as described above.

EXAMPLE 20 cAMP measurements. CHO-$A_3$ or HEK-$A_3$ cells were collected in PBS containing 5 mM EDTA, washed with DMEM and resuspended in DMEM containing adenosine deaminase (1 unit/ml) at a density of 500,000–1,000,000 cells/ml. The cells were kept at room temperature for 0.5–1 hour before the experiments. To start the cAMP measurement, the cell suspension (100 μl) was mixed with 25 μl of test agents and the reaction was kept at 37° C. for 5–30 minutes. The reaction was stopped by addition of 0.2N HCl (125 μl). Cell lysates were centrifuged for 10 minutes at 1000 rpm. The supernatant (100 μl) was collected and acetylated. The concentrations of cAMP in the supernatants were measured using the direct cAMP assay according to the manufacturer's instructions (Assay Design). Alternatively, cells were harvested using 0.0025% trypsin and 2mM EDTA in PBS, washed and resuspended in phenol-free DMEM to a concentration of 1×10$^6$ cells/ml, and then incubated with 1 U/ml of adenosine deaminase for 30 minutes at room temperature. A final concentration of 50 μM of the phosphodiesterase IV inhibitor, rolipram, was added to the cells immediately prior to addition of adenosine receptor agonists, antagonists, and forskolin. After incubating for 5–30 minutes at 37° C., cells were lysed and cAMP concentrations were determined using cAMP-Screen Direct™ System (Applied Biosystem) according to the manufacturer's instructions.

The compounds of Formula I were shown to be potent $A_3$ adenosine receptor agonists in this assay.

What is claimed is:
1. A compound of the formula:

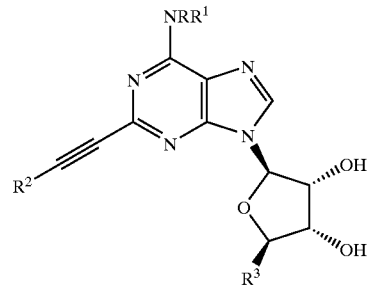

wherein:
R is hydrogen or lower alkyl;
$R^1$ is optionally substituted lower alkoxy or optionally substituted cycloalkyloxy;
$R^2$ is hydrogen, optionally substituted alkyl, optionally substituted cycloalkyl, optionally substituted aryl, optionally substituted heteroaryl, or trialkylsilyl; and
$R^3$ is hydroxymethyl or $R^4R^5NC(O)$—, where $R^4$ and $R^5$ are independently chosen from hydrogen, optionally substituted alkyl or optionally substituted cycloalkyl.
2. The compound of claim 1, wherein $R^3$ is hydroxymethyl.
3. The compound of claim 2, wherein R is hydrogen.
4. The compound of claim 3, wherein $R^1$ is methoxy, ethoxy, n-propoxy, isopropoxy, or cyclopropoxy.
5. The compound of claim 4, wherein $R^1$ is methoxy.
6. The compound of claim 5, wherein $R^2$ is phenyl, namely (4S,2R,3R,5R)-5-(hydroxymethyl)-2-[6-(methoxyamino)-2-(2-phenylethynyl)purin-9-yl]oxolane-3,4-diol.

7. The compound of claim 5, wherein $R^2$ is 4-methylphenyl, namely (4S,2R,3R,5R)-5-hydroxymethyl)-2-[6-(methoxyamino)-2-[(2(4-methylphenyl)ethynyl]purin-9-yl]oxolane-3,4-diol.

8. The compound of claim 5, wherein $R^2$ is 4-fluorophenyl, namely (4S,2R,3R,5R)-2-{2-[2-4-fluorophenyl)ethynyl}-6-(methoxyamino)purin-9-yl}-5-(hydroxymethyl)oxolane-3,4-diol.

9. The compound of claim 5, wherein $R^2$ is 4-pentylphenyl, namely (4S,2R,3R,5R)-5-hydroxymethyl)-2-{6-(methoxyamino)-2-[2-(4-pentylphenylethynyl])purin-9-yl}oxolane-3,4-diol.

10. The compound of claim 5, wherein $R^2$ is 3-trifluromethylphenyl, namely, (4S,2R,3R,5R)-5-(hydroxymethyl)-2-[6-(methoxyamino)-2-[(2(3-trifluoromethyl)phenyl]ethynyl]purin-9-yl]oxolane-3,4-diol.

11. The compound of claim 5, wherein $R^2$ is 4-methoxyphenyl, namely (4S,2R,3R,5R)-5-(hydroxymethyl)-2-[6-(methoxyamino)-2-[(2(4-methoxyphenyl)ethynyl]purin-9-yl]oxolane-3,4-diol.

12. The compound of claim 5, wherein $R^2$ is 4-cyanomethylphenyl, namely 6-{9-2-[4-(2-{9-[4S,2R,3R,5R)-3,4-dihydroxy-5-(hydroxymethyl)oxolan-2-yl]-6-(methoxyamino)-purin-2-yl }ethynyl)phenyl]ethanenitrile.

13. The compound of claim 5, wherein R is butyl, namely (4S,2R,3R,5R)-2-{2-[2-hex-1-ynyl-6-methoxyamino)purin-9-yl }-5-(hydroxymethyl)oxolane-3,4-diol.

14. The compound of claim 5, wherein $R^2$ is 2-hydroxypropyl, namely (4S,2R,3R,5R)-2-[-2-(4-hydroxypent-1-ynyl)-6-(methoxyamino) purin-9-yl}-5-(hydroxymethyl)oxolane-3,4-diol.

15. The compound of claim 5, wherein $R^2$ is 2-hydroxycyclohexyl, namely (4S,2R,3R,5R)-2-[-2-(2-hydroxycyclohexyl-1-ynyl)-6-(methoxyamino) purin-9-yl}-5-(hydroxymethyl)oxolane-3,4-diol.

16. The compound of claim 5, wherein $R^2$ is 2-pyridyl, namely (4S,2R,3R,5R)-5-(hydroxymethyl)-2-[6-(methoxyamino)-2-[(2-(2-pyridyl) ethynyl) purin-9-yl] oxolane-3,4-diol.

17. The compound of claim 1, wherein $R^3$ is $R^4R^5NC(O)$—.

18. The compound of claim 17, wherein R is hydrogen.

19. The compound of claim 18, wherein $R^1$ is methoxy.

20. The compound of claim 19, wherein $R^4$ is hydrogen and $R^5$ is methyl or ethyl.

21. The compound of claim 20, wherein $R^2$ is optionally substituted phenyl or optionally substituted pyridyl.

22. The compound of claim 21, wherein $R^2$ is phenyl, 4-methylphenyl, 4-fluorophenyl, 3-trifluoromethylphenyl, 4-methoxyphenyl, 2-pyridyl, 3-pyridyl, or 4-pyridyl.

23. A method of treating a disease state by stimulating adenosine $A_3$ receptors, comprising administering to a mammal in need thereof a therapeutically effective dose of a compound of claim 1.

24. A pharmaceutical composition comprising at least one pharmaceutically acceptable excipient and a therapeutically effective amount of a compound of claim 1.

* * * * *